US00PP15258P2

(12) United States Plant Patent
Schlueter

(10) Patent No.: US PP15,258 P2
(45) Date of Patent: Oct. 19, 2004

(54) ***HIBISCUS ROSA-SINENSIS* PLANT NAMED 'FOREVER YOUNG'**

(50) Latin Name: *Hibiscus rosa-sinensis*
Varietal Denomination: Forever Young

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/764,156

(22) Filed: Jan. 23, 2004

(51) Int. Cl.[7] ..... A01H 5/00
(52) U.S. Cl. ..... Plt./257
(58) Field of Search ..... Plt./257

*Primary Examiner*—Kent Bell
(74) *Attorney, Agent, or Firm*—Christie, Parker & Hale, LLP

(57) ABSTRACT

A new plant variety of *Hibiscus rosa-sinensis* named 'Forever Young', characterized by a large fuchsia-pink flower with a red eye and white veining throughout, and with petals that curve along the edges. It is a free-flowering plant with an upright, compact habit. The foliage is glossy and dark green.

4 Drawing Sheets

Botanical classification: *Hibiscus rosa-sinensis* L.
Varietal denomination: The new plant has the varietal denomination 'Forever Young'.

BACKGROUND OF THE INVENTION

The present invention relates to a new and distinct variety of *Hibiscus rosa-sinensis* L., which was developed in a controlled breeding program in Webster, Tex.

The genus *Hibiscus* comprises about 250 species of herbs, shrubs and trees in warm temperate and tropical regions; with leaves usually simple, mostly palmately veined, lobed or parted; flowers mostly solitary in the leaf axils but sometimes in racemes, corymbs or panicles. *Hibiscus* is included in the family Malvaceae, which comprises about 95 genera of herbs, shrubs and trees originating in tropical and temperature regions. *Hibiscus rosa-sinensis* is a glabrate shrub, seldom over 8 feet tall in cultivation, but treelike to 15 feet or more in tropical regions. Leaves to 6-inches long, ovate, usually serrate, mostly glossy green. Flowers solitary in upper leaf axils.

The new *Hibiscus* is a product of a planned breeding program conducted by the inventor in Webster, Tex. The objective of the program was to create new Hibiscus selections with improved bloom quality, color and floriferousness, plants that can be commercially produced on their own root systems, and improved plant habit with regard to vigor and postproduction longevity.

The new *Hibiscus* originated from a cross-pollination made by the Inventor using 'Miss Liberty' (not patented) as the female parent and 'Jazz' (not patented) as the male parent. The new *Hibiscus* was discovered and selected by the Inventor as a plant within the progeny of the stated cross-pollination in a controlled breeding program in Webster, Tex.

SUMMARY OF THE INVENTION

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy green foliage;
3. Vigorous growth habit;
4. Large fuchsia-pink flower with a red eye, white veining throughout, and petals that curve back along the edges;
5. Free-flowering.

Asexual reproduction of the new variety by stem cuttings, performed in Webster, Tex. and Fulshear, Tex. have confirmed that the distinctive characteristics of the new variety are stable and transmitted to succeeding generations, and the new variety reproduces true to type.

COMPARISON WITH PARENTS AND OTHER CULTIVARS

'Forever Young' is distinguished from its female parent 'Miss Liberty' (not patented) by having fuchsia-pink petals with white veining; flowers of 'Miss Liberty' have scarlet petals with white spots, and have white eyes. 'Forever Young' is distinguished from its male parent 'Jazz' (not patented) by its flower color; 'Jazz' has a flashy bloom with orange, yellow and shiny metallic hues.

Plants of 'Forever Young' can be compared to plants of the cultivar 'Erika Nicole' (not patented). However, in side-by-side comparisons conducted in Webster, Tex., plants of 'Forever Young' differ from plants of the cultivar 'Erika Nicole' in the following characteristics:

1. Flowers of 'Forever Young' brighter in color than flowers of 'Erika Nicole';
2. Plants of 'Forever Young' are easier to propagate via vegetative cuttings than plants of the cultivar 'Erika Nicole';

BRIEF DESCRIPTION OF ILLUSTRATIONS

The accompanying illustrations show a specimen of the new cultivar in a photographic illustration as true to color as is reasonably possible to make in an illustration of this character.

DETAILED DESCRIPTION OF THE NEW VARIETY

Figure 1:
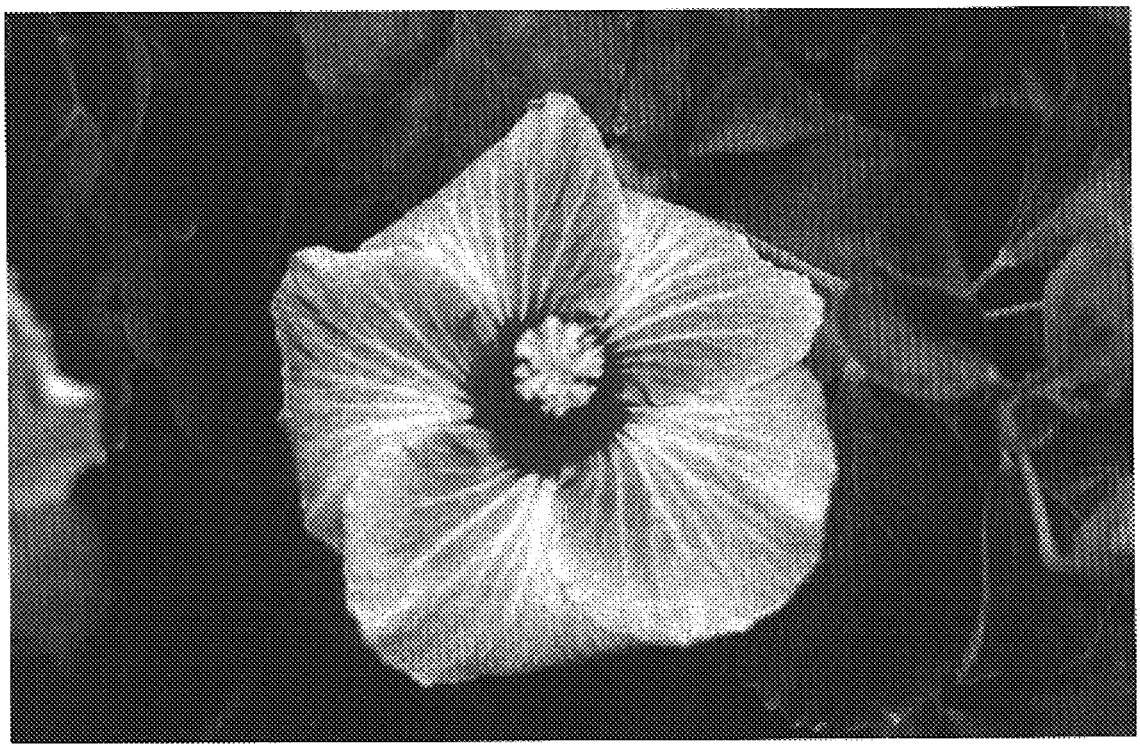
FIG. 1 illustrates a side perspective view of a typical plant of 'Forever Young'.
Figure 2:
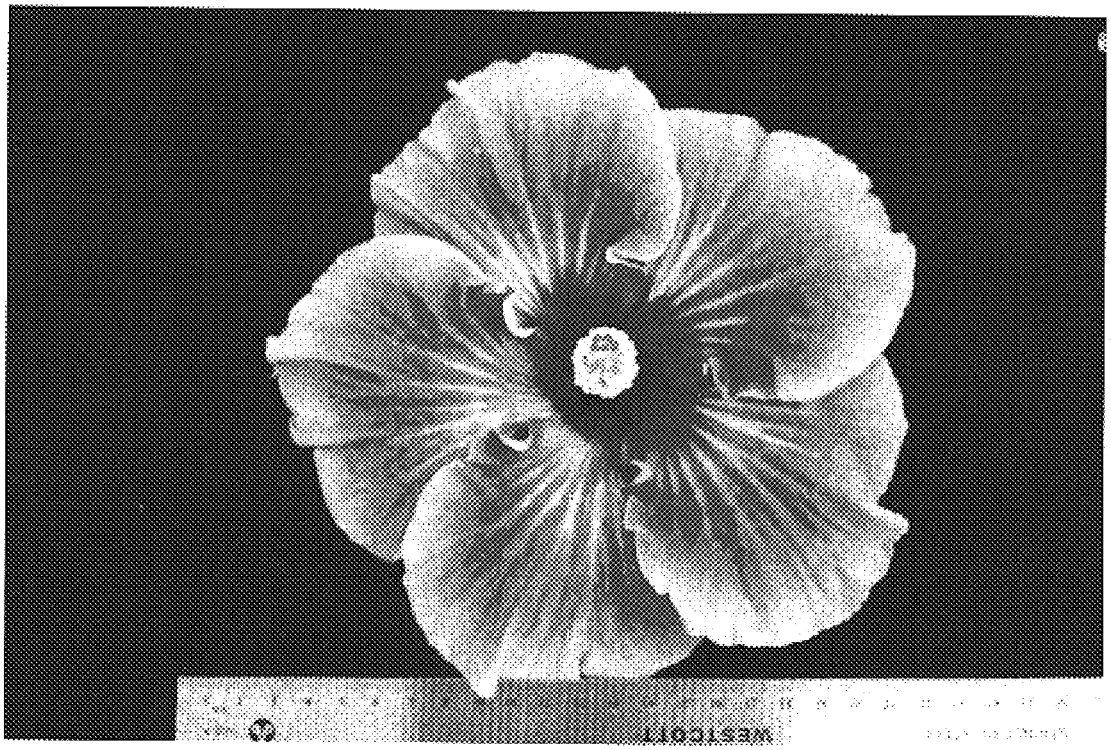
FIG. 2 illustrates the scale of a typical flower of 'Forever Young'.
Figure 3:
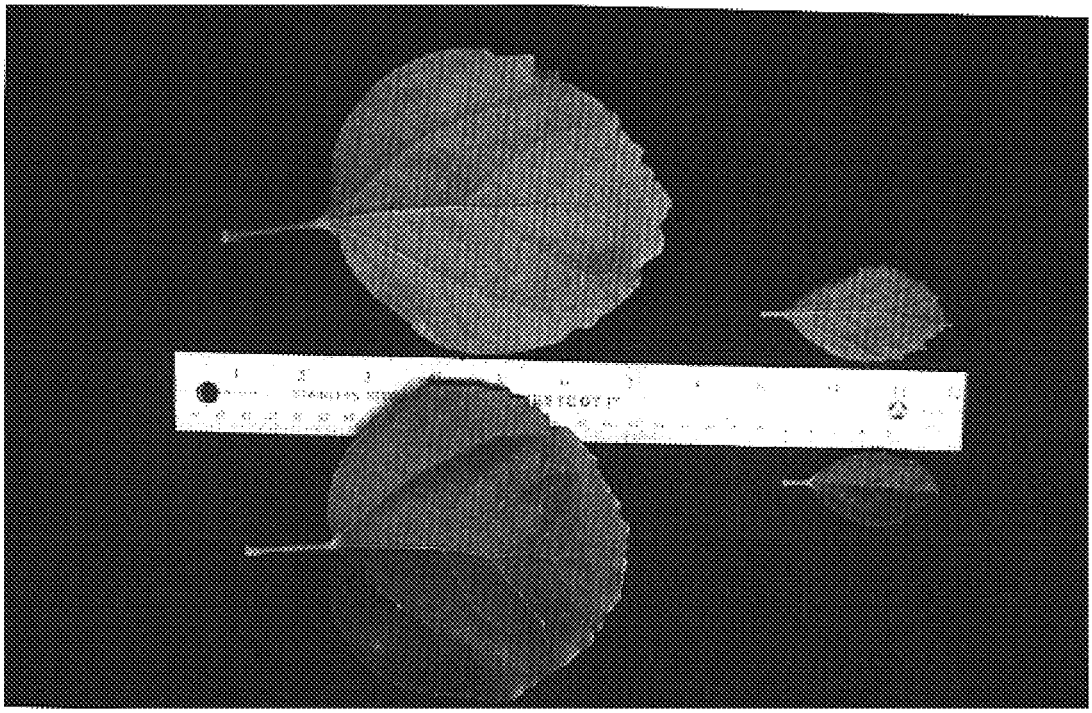
FIG. 3 illustrates the typical young to mature foliage of 'Forever Young'; the abaxial and adaxial surfaces are shown at each stage.
Figure 4:
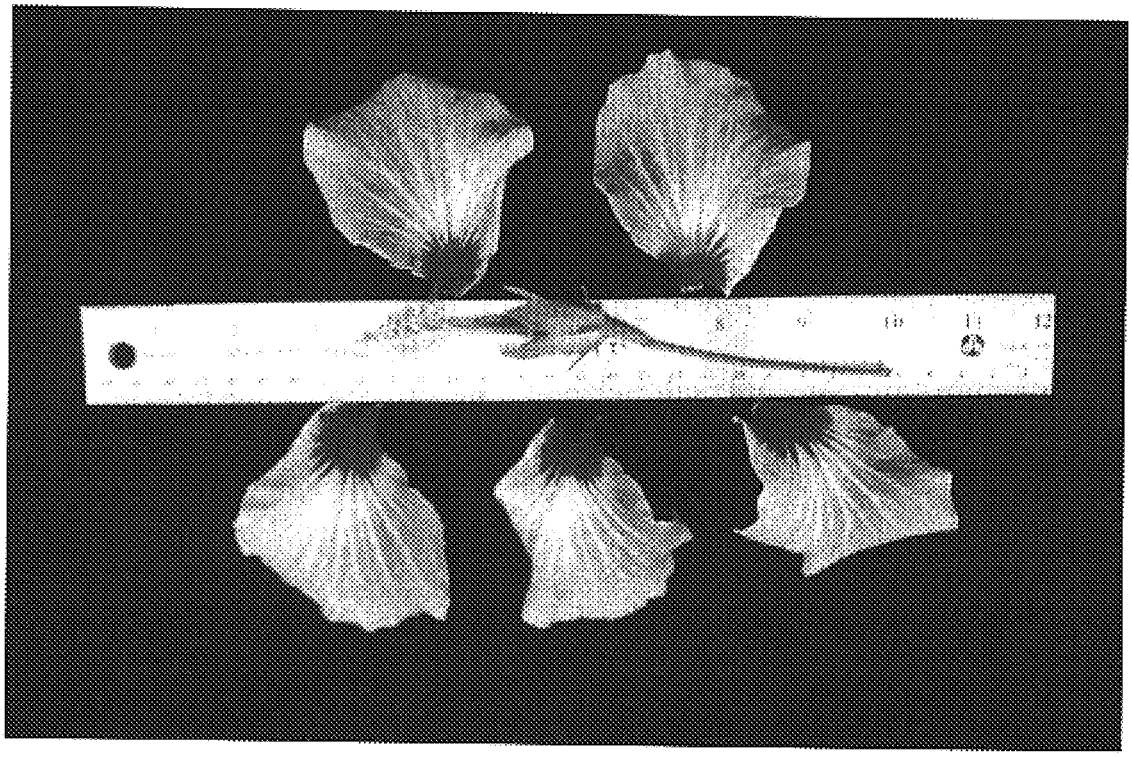
FIG. 4 illustrates a dissected flower of 'Forever Young', including shape and size of petals and characteristics of the reproductive structures.

'Forever Young' has not been observed under all possible environmental, cultural and light conditions. The following observations and descriptions are of plants grown in Fulshear, Tex., in February 2003, under polypropylene shadecloth providing a 30 percent light reduction, and under conditions which closely approximate commercial production. Plants described were approximately one year old and in a #3 nursery container. In this description, color references are to The Royal Horticultural Society Colour Chart (2000) and terminology used in the color descriptions herein refers to plate numbers in this color chart. Phenotypic expression may vary with light intensity, cultural and environmental conditions.

CLASSIFICATION

Botanical: *Hibiscus rosa-sinensis* L. 'Forever Young'.
Parentage:
- *Female or seed parent.*—*Hibiscus rosa-sinensis* 'Miss Liberty' (not patented).
- *Male or pollen parent.*—*Hibiscus rosa-sinensis* 'Jazz' (not patented).

Propagation: By stem cuttings.
Time to initiate rooting: Approximately 14 to 21 days at 21–24 C.
Time to develop roots: Approximately 42 to 56 days at 21–24 C.
Root description: Fine to medium; fibrous; freely branching.

PLANT

Size:
- *Height.*—Approximately 51 cm from soil level to top of flowers.
- *Diameter/spread.*—Approximately 60 cm.

Form and growth habit: Perennial, evergreen shrub; mostly upright and somewhat spreading.
Branching: Freely branching; approximately 4 to 8 lateral branches develop after pinching.
- *Lateral branches.*—Approximately 20 cm long and 5 mm in diameter.
- *Internode length.*—Approximately 4 cm.

LEAF

Shape: Ovate.
- *Apex.*—Acute.
- *Base.*—Cordate.

Leaf size: Approximately 12 cm long and 12 cm wide.
Arrangement: Alternate, single; symmetrical.
Margin: Crenate.
Aspect: Undulate.
Texture/substance: Glabrous, shiny.
Coloration:
- *Young foliage.*—Upper side: Near Yellow-Green Group 146A. Under side: New Yellow-Green Group 146B.
- *Mature foliage.*—Upper side: Near Green Group 147A. Under side: Near Green Group 147B.

Petioles:
- *Size.*—Approximately 3 cm long, 3 mm across.
- *Coloration.*—Near Yellow-Green Group 146A.
- *Texture.*—Smooth.

Hardiness: USDA Zone 10 (30° F. to 40° F.).
Pests/diseases: Resistance to known *Hibiscus* diseases had not been observed on plants grown under conditions approximating commercial practices.

INFLORESENCE

Bloom period: Typically year-round under subtropical and tropical conditions.
Flower arrangement: Arranged singly at terminal leaf axils; free-flowering with 3 to 4 flower buds and/or open flowers per terminal apex; flowers face upright and slightly outward.
Flower appearance: Fuchsia-pink petals with a red eye and white veins radiating from the center; flowers are open for about two days before closing; flowers persistent.
Flower diameter: Approximately 16 cm.
Buds (just prior to showing color):
- *Rate of opening.*—Approximately 1 or 2 days, depending on temperature.
- *Shape.*—Elliptic.
- *Length.*—Approximately 3 cm.
- *Diameter.*—Approximately 1.5 cm.
- *Color.*—Near Yellow-Green Group 146B.

Fragrance: None noted.
Petals:
- *Number/arrangement.*—Corolla consists of 5 overlapping petals.
- *Shape.*—Spatulate with rounded apex.
- *Size.*—Approximately 8.5 cm long and 8.5 cm wide.
- *Margin.*—Entire, but ruffled.
- *Texture.*—Smooth.
- *Color.*—Upper Surface: The "eye" or throat starts near Red Group 46A and transitions outward to near Red Group 55A, 55B and 55C. Veining is near White Group N155A. Lower Surface: The lower two-thirds of the petal is near White Group N155C, with the edges darkening to near Red Group 55B and 55C.

Sepals:
- *Number/arrangement.*—5 sepals fused into a star-shaped calyx.
- *Shape.*—Linear with acuminate apices.
- *Margin.*—Entire.
- *Color.*—Near Yellow-Green Group 146A.

Peduncles:
- *Length.*—Approximately 6 cm.
- *Diameter.*—Approximately 2 mm.
- *Angle.*—Upright to about 45 degrees.
- *Strength.*—Strong, flexible.
- *Color.*—Near Yellow-Green Group 144A.

REPRODUCTIVE ORGANS

Androecium:
- *Stamens.*—Numerous; approximately 50. Stamen Length: Approximately 5 mm. Filament Color: Near Red Group 56B.
- *Anther length.*—Approximately 2 mm.
- *Pollen amount.*—Abundant.
- *Pollen color.*—Yellow-Orange Group 15B.

Gynoecium:
- *Pistil number.*—1.

*Pistil length.*—Approximately 6.5 cm.
*Stigma appearance.*—5, rounded.
*Stigma diameter.*—Approximately 2 mm.
*Stigma color.*—Near Orange-Red Group 33A.
*Style color.*—Lower third near Red Group 46A; mid-third near Red Group 48C; upper third near Red Group 49C.
*Seed production.*—Seed production has not been observed.

I claim:

1. A new variety of *Hibiscus rosa-sinensis* plant as shown and described.

* * * * *